United States Patent
Zuelli et al.

(10) Patent No.: US 6,558,941 B2
(45) Date of Patent: May 6, 2003

(54) DELIVERING LIPOPHILIC SUBSTANCES INTO CELLS USING NANOEMULSIONS

(75) Inventors: Fred Zuelli, Küttigen (CH); Franz Suter, Doettingen (CH)

(73) Assignee: Mibelle AG Cosmetics, Buchs/AG (CH)

( * ) Notice: Subject to any disclaimer, the term of this patent is extended or adjusted under 35 U.S.C. 154(b) by 0 days.

(21) Appl. No.: 09/896,239

(22) Filed: Jun. 29, 2001

(65) Prior Publication Data

US 2002/0132284 A1 Sep. 19, 2002

Related U.S. Application Data

(62) Division of application No. 09/262,516, filed on Mar. 4, 1999, now Pat. No. 6,265,180.

(30) Foreign Application Priority Data

Mar. 30, 1998 (CH) ................................ 0748/98

(51) Int. Cl.[7] .......................... C12N 1/38; C12N 5/00; C12N 1/00; C12P 1/00; C12P 21/06
(52) U.S. Cl. ........................... 435/244; 435/29; 435/41; 435/69.1; 435/71.1; 435/134; 435/243; 435/325; 435/375; 435/377; 435/404; 435/405
(58) Field of Search ........................... 435/29, 41, 69.1, 435/71.1, 134, 325, 375, 377, 404, 405, 243, 244

(56) References Cited

U.S. PATENT DOCUMENTS

| | | | | |
|---|---|---|---|---|
| 5,152,923 A | | 10/1992 | Weder et al. | ................ 252/312 |
| 5,372,943 A | * | 12/1994 | Inlow et al. | ................ 435/404 |
| 5,658,575 A | | 8/1997 | Ribier et al. | ................ 424/401 |

\* cited by examiner

*Primary Examiner*—David M. Naff
(74) *Attorney, Agent, or Firm*—Tarolli, Sundheim, Covell & Tummino, L.L.P.

(57) ABSTRACT

Nanoemulsions are prepared containing oily droplets of a diameter of less than 100 nm in an aqueous phase. The oily droplets contain a lipophilic substance, and have on their surface an amphoteric emulsifier in an amount of preferably 0.65 to 0.75 parts by weight amphoteric emulsifier for one part by weight of oily component forming the droplets. The oily component of the droplets is preferably a triglyceride containing oleic acid and/or linoleic acid. The nanoemulsions, which may be sterile, are used for delivering into cells the lipophilic substance contained by the oily droplets. This delivery can be used to biotransform the lipophilic substance, promote cell differentiation, growth or biosynthesis of a desired substance, or to test for toxicity of the lipophilic substance.

2 Claims, 2 Drawing Sheets

DELIVERING LIPOPHILIC SUBSTANCES INTO CELLS USING NANOEMULSIONS

This application is a division of application Ser. No. 09/262,516, filed Mar. 4, 1999, now U.S. Pat. No. 6,265,180.

FIELD OF THE INVENTION

This invention relates to methods for completing a cell culture medium with a lipophilic substance promoting growth of cells by weight or promoting the biosythesis of desired substances within the cells, and to nanoemulsions suitable in said methods.

BACKGROUND OF THE INVENTION

Nanoemulsions, alternatively called nanoparticles, are composed of oil particles, the surfaces of which are occupied by an amphoteric emulsifier in aqueous dispersions. They can be prepared by mixing triglycerides or fatty acid esters in aqueous phase using a high pressure homogenizer (EP-B1-0 406 162—H. G. Weder).

So far, they were used for the manufacture of pharmaceutical and/or cosmetic preparations, and also for the preparation of nutrient solutions in which the nanoemulsions serve as the energy supplier in cell cultures (EP-B1-0 406 162—H. G. Weder).

The cell culture technique is a biological system having a very wide application. Controlled culturing of these cells is mainly used in immunology, in biotechnology, in toxicology, in gene technology, and in cell biology. In all said applications the interaction of substances with cells is of primary importance. The exchange of biochemical substances with the cells takes place in the culture medium which is composed of a large number of different substances. In order to create ideal conditions for the cells, in most cases blood serum is added to the culture medium. However, for many uses the complementation of said medium with blood serum shows severe disadvantages, since the blood serum has an undefined composition, is expensive, and may contain undesired components, such as viruses, prions and germs. Therefore, for many applications the creation of so-called serum-free media is of primary importance.

Working with cell cultures, a general difficulty is the application of test substances which are insoluble in water. If possible, lipophilic substances are dissolved in alcohol or dimethylsulfoxide, and then added to the culture medium. However, this results in undefined dispersions of said substances having a low bioavailability. The use of solubilizers, such as Tween 20®, results in unstable and very toxic emulsions.

Therefore, no reliable and simple methods were so far available to solve the following problems:

Completion of cell culture media with lipophilic substances promoting cell growth;
Completion of cell culture media with lipophilic substances promoting biosynthesis of desired substances within the cells.

OBJECTS OF THE INVENTION

It is the primary object of the invention to solve the above mentioned problems by creating methods for delivering lipophilic substances to cell cultures, which lipophilic substances promote the growth of cells by weight or promote the biosynthesis of desired substances within the cells, by using nanoemulsions as vehicle.

The foregoing and further objects, advantages and features will be apparent from the following specification.

SUMMARY OF THE INVENTION

To meet these and other objects, the invention provides the following methods, and the following dispersions suitable for use in these methods:

a method of completing a cell culture medium with a lipophilic substance promoting the growth of cells by weight, said method comprising the steps of: (a) preparing a dispersion consisting of a nanoemulsion containing the substance promoting the growth of cells, in aqueous phase; and (b) adding said dispersion to said cell culture;

a method of completing a cell culture medium with a lipophilic substance promoting the biosynthesis of desired substances within the cells, said method comprising the steps of: (a) preparing a dispersion consisting of a nanoemulsion containing the substance promoting said biosynthesis, in aqueous phase; and (b) adding said dispersion to said cell culture.

Preferably, said dispersions comprise as oily component a triglyceride of the fatty acids C 18:1 (oleic acid) and/or C 18:2 (linoleic acid), and comprise nanoemulsions comprising from 0.65 to 0.75 parts by weight of said amphoteric emulsifier for one part by weight of said oily component.

BRIEF DESCRIPTION OF THE DRAWINGS

Other characteristics and advantages of the invention will appear from the description which follows, given by way of example and with reference to the attached drawings in which.

DESCRIPTION OF PREFERRED EMBODIMENTS

Figure 1:
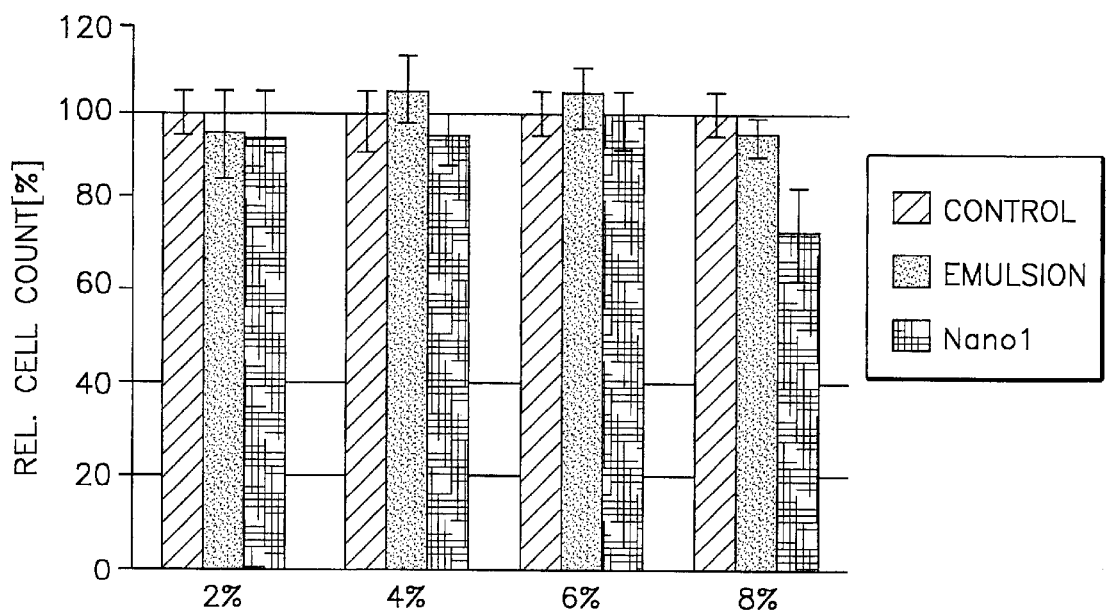
FIG. 1 is a representation of the relative cell number as a function of different concentrations of Nanoemulsion 1 ("Nano 1" of Example 1) and liposomes comprising the emulsifier "Emul"). These relative cell numbers are compared with untreated cultures ("Kontr" is 100%).

Nanoemulsions useful in the present invention can easily be prepared by mixing the ingredients together and passing the mixture through a high pressure homogenizer.

Preferably, the oily particles of the nanoemulsion have a diameter of less than 100 nm, and particularly of less than 40 nm, and preferably their surface is bearing the amphoteric emulsifier as a monolayer.

Preferably, the nanoemulsions have a negative zeta-potential, particularly between −10 mV and −50 mV, and especially between −30 mV and −40 mV. However, for special applications nanoemulsions having a positive zeta-potential may be advantageous. Such cationic nanoemulsions can e.g. be obtained by addition of a C8- to C22-alkylamine.

Preferably, the nanoemulsions contain more than 0.4 parts by weight, and particularly 0.45 to 0.75 parts by weight, of the amphoteric emulsifier per one part by weight of oil. As a general rule, the diameter of the oil particles increases as the portion of the amphoteric emulsifier decreases.

Preferably, the amphoteric emulsifier itself has a low toxicity to cell cultures, and preferably lecithin is used for this purpose.

Preferably, the oil phase as well has a low toxicity to cell cultures, and particularly such a low toxicity that the growth of the cell culture is reduced for less than 20% as compared to a reference culture containing no oily component.

Particularly useful for this purpose are natural triglycerides, and especially natural triglycerides of the fatty acid C 18:1 (oleic acid) and/or the fatty acid C 18:2 (linoleic acid). Said fatty acid have a very low toxicity and are particularly useful as solvent for lipophilic test substances.

As said above, the nanoemulsions can be prepared by high pressure homogenization of premixes of the ingredients. Preferably, the ratio of lecithin to oil is higher than 0.41. Optimal mixtures e.g. have a ratio of 0.6. Furthermore, it is of great advantage if the nanoemulsions have a small particle diameter. Oil-in-water emulsions comprising oil droplets which are smaller than 70 nm are transparent. Such transparent nanoemulsions facilitate visual control of the cell cultures. Moreover, dispersions of a small average particle size (e.g. 100 nm) can easily be sterilized by filtration.

Nanoemulsions are very stable and can be stored in a refrigerator for months before being added to the cell cultures.

Preferred embodiments of the invention are described and explained in the following examples and the annexed drawings.

EXAMPLE 1

Treatment of TK6-Lymphoblastid Cells With a Nanoemulsion Having a Low Toxicity

TK6-cells were cultivated in a RPMI-1640 medium, which was completed with 2 mmol of glutamine, 5% of gentamycin and 10% of horse serum. The cell suspension was inoculated into new cell culture flasks every 2 to 3 days. The number of cells was determined by means of a Neubauer chamber. The influence of Nano emulsion 1 and of the void lecithin particles (liposomes) on the cell growth was determined for different concentrations after 2 days.

FIG. 1 shows the relative cell numbers compared to untreated cells ("Contr" is 100%). Nanoemulsion 1 ("Nano 1") has no influence on the cell growth up to a concentration of 6%. The emulsifier ("Emul") has even no influence on the relative cell number up to a concentration of 8%.

Figure 2:
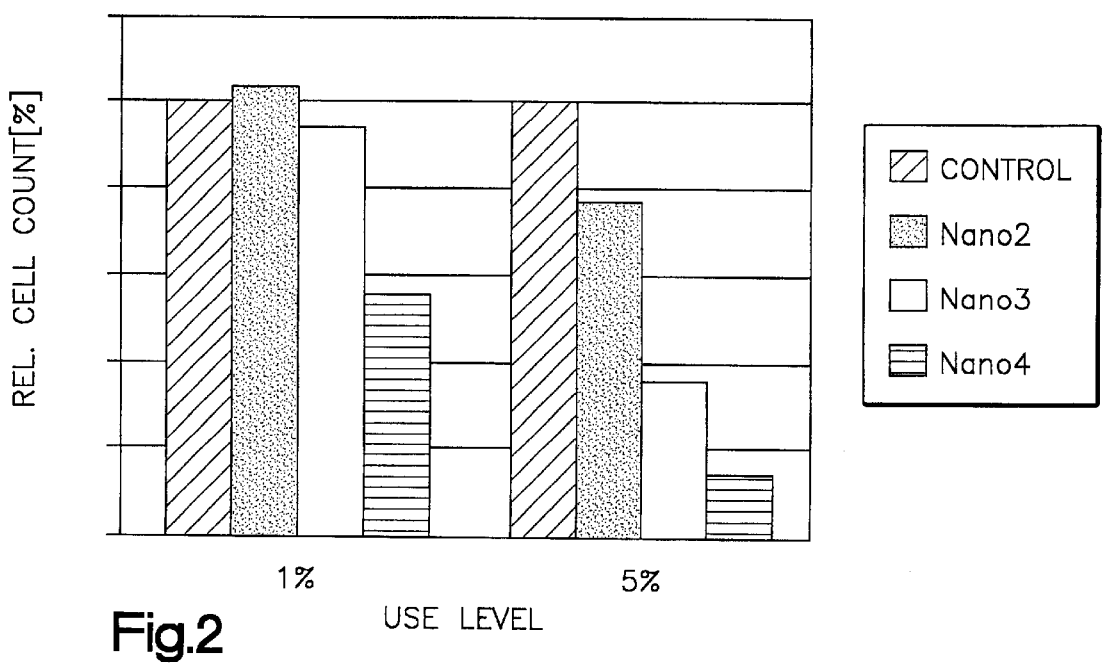
FIG. 2 is a representation of the relative cell number as a function of various amounts of three different nanoemulsions ("Nano 2", "Nano 3" and "Nano 4" of Example 1). These relative cell numbers are compared with untreated cultures ("Kontr" is 100%).

FIG. 2 shows that nanoemulsions comprising other oil components are essentially more toxic than the oil in Nanoemulsion 1 when using the same concentration and the same emulsifier. In FIG. 2, the oil components are sunflower oil ("Nano 2), hydrogenated peanut oil ("Nano 3"), and a saturated C 8/10 triglyceride ("Nano 4").

| Composition of Nanoemulsion 1 | |
|---|---|
| Lecithin | 0.6% |
| Triglyceride | 1.0% |
| of which: | 90% C 18:1 and 10% C 18:2 |
| Particle diameter | 41 nm |
| Composition of Nanoemulsion 2 | |
| Lecithin | 0.6% |
| Sunflower oil | 1.0% |
| Particle diameter | 45 nm |
| Composition of Nanoemulsion 3 | |
| Lecithin | 0.6% |
| Hydrogenated peanut oil | 1.0% |
| Particle diameter | 50 nm |
| Composition of Nanoemulsion 5 | |
| Lecithin | 0.6% |
| Caprylic acid/capric acid triglyceride | 1.0% |
| Particle diameter | 45 nm |

EXAMPLE 2

Figure 3:
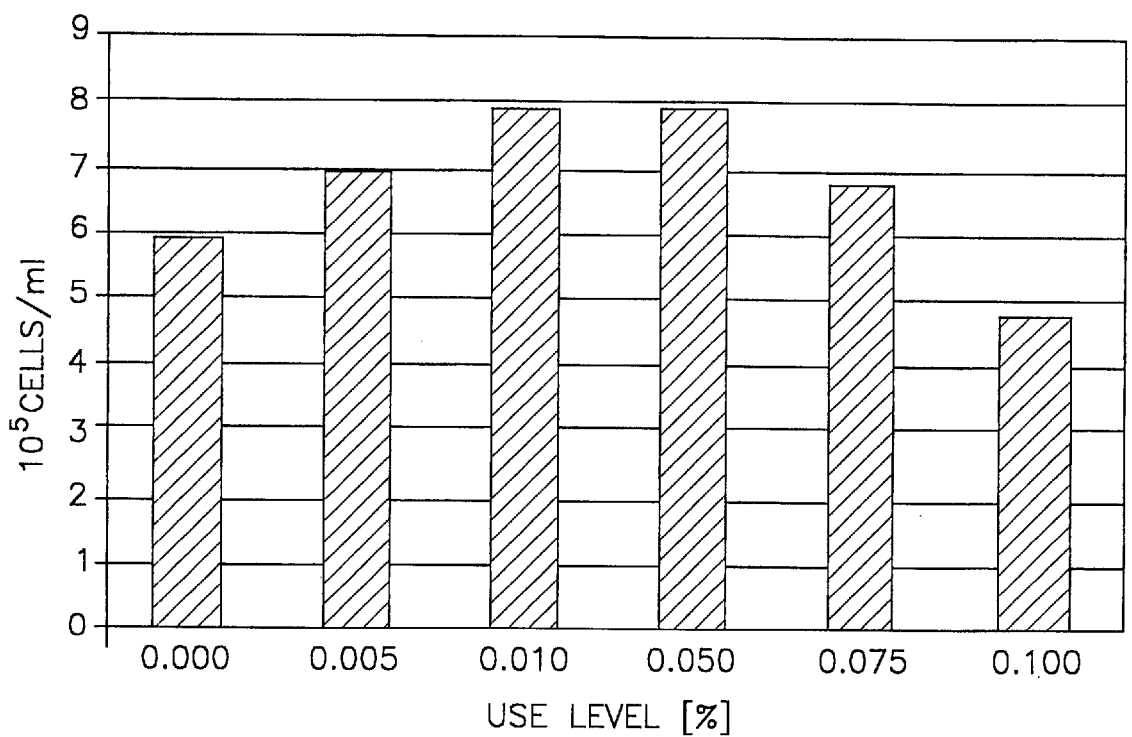
FIG. 3 is a representation of the number of cells per ml as a function of the addition of different amounts of nanoemulsion 5 of Example 2 to the culture medium.

Use of a Nanoemulsion Containing Vitamins A and E for Completing a Serum-Free Cell Culture Media in Order to Promote Cell Growth Hybridoma cells producing a specific antibody were cultivated in an serum-free medium (Cell Culture Technologies). Cell growth could be improved by the addition of Nano emulsion 5 (FIG. 3).

| Composition of Nanoemulsion 5 | |
|---|---|
| Lecithin | 0.6% |
| Caprylic acid/capric acid triglyceride | 0.6% |
| Vitamin E acetate | 0.3% |
| Vitamin A palmitate | 0.1% |
| Particle diameter | 45 nm |

EXAMPLE 3

Figure 4:
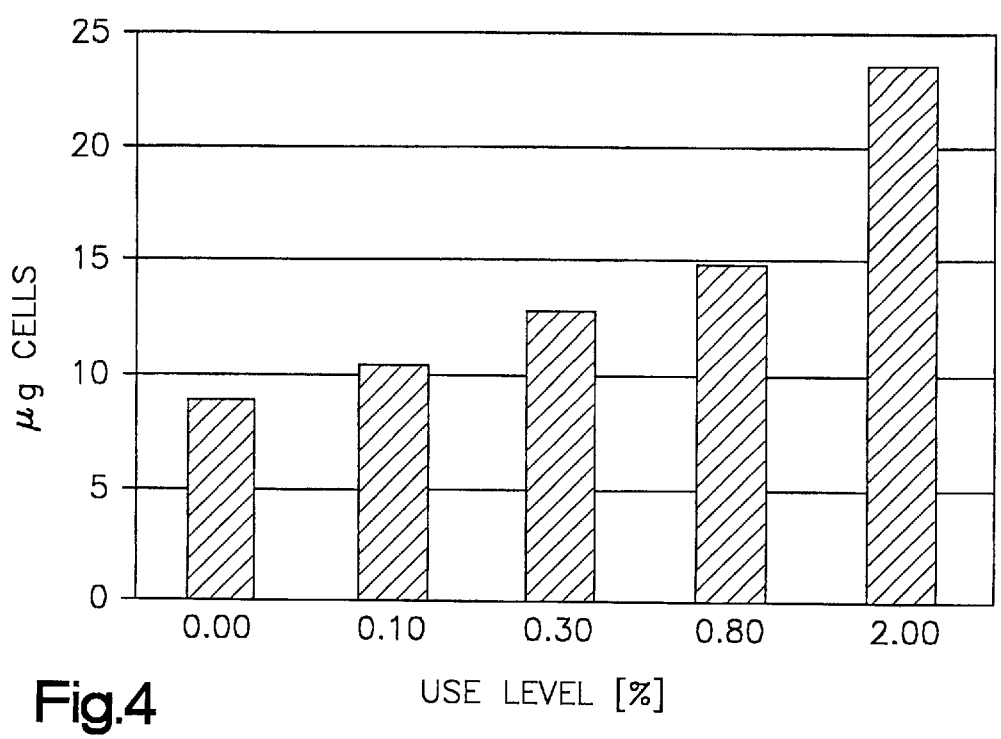
FIG. 4 is a representation of the amount of cells in microgram obtained in a culture which contained different amounts of nanoemulsion 5 of Example 2.

Completion of a Serum-Free Cell Culture of Fibroblasts by a Nanoemulsion in Order to Increase the Biomass Production Balb-3T3 fibroblasts were cultivated in serum-free DMEM/F12-(1:1) medium (BioConcept) at various concentrations of Nanoemulsion 5. The 50 ml cultures were harvested after 9 days, and the biomass was determined (FIG. 4).

EXAMPLE 4

Use of Nanoemulsions Containing Unsaturated Fatty Acids, Vitamins and β-Carotene in Order to Promote the Biosynthesis of Specific Antibodies in Hybridoma Cells in Serum-Free Medium Serum-free medium are particularly suitable for the production of proteins, since they do not contain any foreign proteins which could affect the isolation of the products. However in serum-free cell cultures essential lipophilic substances, such as unsaturated fatty acids and vitamins, normally present in the serum are often lacking. These substances cannot be added without hesitation to the serum-free medium, since they are water-insoluble, difficult to be dispersed in a controlled manner, and show only a low bioavailability. By completing these media with nanoemulsions containing essential lipids (e.g. Nanoemulsion 6) e.g. the production of specific antibodies in hybridoma cells can be improved substantially.

| Composition of Nanoemulsion 6 | |
| --- | --- |
| Lecithin | 0.30% |
| Triglyceride | 0.50% |
| Of which: | 90% |
| | C 18:1 |
| | and |
| | 10% |
| | C 18:2 |
| α-Tocopheral | 0.0100% |
| Vitamin A acetate | 0.0050% |
| Linoleic acid | 0.0100% |
| Linolenic acid | 0.0100% |
| β-Carotene | 0.0001% |
| Particle diameter | 65 nm |

EXAMPLE 5

Use of Nanoemulsions for Promoting the Biosynthesis of Recombinant Proteins

CHO-cells (Chinese Hamster Ovary Cells) are often used for the production of recombinant proteins, such as growth factors, blood coagulation factors, and cytokines. Thereby, the biosynthesis of these products in serum-free media can be improved by addition of nanoemulsions containing essential lipophilic substances (e.g. Nanoemulsion 5).

EXAMPLE 6

Use of Nanoemulsions in Perfusion Systems

Nanoemulsion 5 can also be used for increasing the interferon-β secretion of fibroblasts which are cultivated in a perfusion system.

From the above description of the invention, those skilled in the art will perceive improvements, changes and modifications. Such improvements, changes and modifications within the skill of the art are intended to be covered by the appended claims.

Having described the invention, the following is claimed:

1. A method of preparing a cell culture medium containing a lipophilic substance promoting the growth of cells, said method comprising the steps of:

(a) preparing a dispersion comprising a nanoemulsion; and (b) adding said dispersion to said cell culture medium;

said nanoemulsion including;

a lipophilic substance promoting the growth of cells and an oily component consisting of droplets dispersed in an aqueous phase, the oily droplets containing the lipophilic substance, the surface of the oily droplets comprising a non-toxic amphoteric emulsifier, the oily droplets having a diameter of less than 100 nm, and the nanoemulsion comprising from 0.65 to 0.75 parts by weight of amphoteric emulsifier for one part by weight of the oily component.

2. A method of preparing a cell culture medium containing a lipophilic substance promoting the biosynthesis of desired substances within cells cultured in the medium, said method comprising the steps of:

(a) preparing a dispersion comprising a nanoemulsion; and (b) adding said dispersion to said cell culture medium;

said nanoemulsion including;

a lipophilic substance promoting said biosynthesis and an oily component consisting of droplets dispersed in aqueous phase, the oily droplets containing the lipophilic substance, the surface of the oily droplets comprising a non-toxic amphoteric emulsifier, the oily droplets having a diameter of less than 100 nm, and the nanoemulsion comprising from 0.65 to 0.75 parts by weight of amphoteric emulsifier for one part by weight of the oily component.

* * * * *